United States Patent [19]

Törnmarck

[11] 3,977,945

[45] Aug. 31, 1976

[54] TIME AND TEMPERATURE-DEPENDENT ENZYMATIC INDICATOR

[75] Inventor: Sven Ivan Arvid Törnmarck, Malmo, Sweden

[73] Assignee: Food Control AB, Malmo, Sweden

[22] Filed: Feb. 20, 1975

[21] Appl. No.: 551,439

[30] Foreign Application Priority Data
Feb. 21, 1974 Sweden.............................. 7402282

[52] U.S. Cl.................................... 195/127; 195/63; 195/103.5 R; 426/61; 426/88; 426/231; 426/524

[51] Int. Cl.²....................... C12K 1/04; C12K 1/00; A23L 3/00; G01N 31/14

[58] Field of Search ............... 426/88, 127, 61, 231, 426/524; 195/103.5 R, 63, 127

[56] References Cited
UNITED STATES PATENTS

| | | | |
|---|---|---|---|
| 2,671,028 | 3/1954 | Clark | 195/63 |
| 3,822,189 | 7/1974 | Tornmarck | 195/103.5 R |
| 3,846,242 | 11/1974 | Ernst | 195/103.5 R |

*Primary Examiner*—David M. Naff
*Assistant Examiner*—C. A. Fan
*Attorney, Agent, or Firm*—Beveridge, DeGrandi, Kline & Lunsford

[57] ABSTRACT

A time and temperature dependent enzymatic indicator with discontinuable indication comprises a plastic envelope container enclosing an enzyme, an enzymatic substrate and a $p$H-indicator as active components, the indication being discontinuable in that the enzyme is bound to a carrier and in that the plastic envelope is sealable for dividing the container into two compartments, one of which is free from enzyme and thus cannot provide further indication.

9 Claims, 6 Drawing Figures

TIME AND TEMPERATURE-DEPENDENT ENZYMATIC INDICATOR

The present invention relates generally to time and temperature-dependent enzymatic indicators and more particularly to an indicator of the above type in which the indication can be discontinued at any desired point of time.

Time and temperature-dependent indicators, such as enzymatic indicators, are previously known from, for example, U.S. Pat. No. 2,671,028. Such indicators are primarily intended for the visual indication of the storage conditions of food to show whether or not the food in question has been stored under unsuitable circumstances, for example, at too high a temperature and/or for too long a time. This is particularly important for deep-frozen foodstuffs since it is difficult or impossible to determine in any other manner whether or not these deep-frozen foodstuffs have been stored in a satisfactory way. The indication obtained with the prior art enzymatic indicators is irreversible, that is to say, it cannot be returned to its initial state. The intention with this is that it should not be possible to manipulate the indicator which, instead, when applied to a packet of foodstuffs should provide a complete and objective indication of the time and temperature conditions to which the foodstuff has been subjected from its production to its purchase by the consumer. One of the most important prerequisites in the prior art indicators has thus been that it should not be possible to discontinue the indication which, instead, should continue until the consumption of the foodstuff.

However, it has been found that there is a need for an indicator of the above stated type, in which it should be possible to discontinue the indication at any desired point of time. The reason for this is that storage-sensitive, perishable goods, such as foodstuffs, pass through many different links in the chain from production to consumption. For example, the product is first manufactured and stored by the manufacturer, then transported by a supplier to a wholesaler for further storage, to be thereafter transported once more to the retailer for final storage and sale to the consumer. If, when the product is sold to the consumer, it appears from the indication displayed by the indicator that the product has been subjected to unsatisfactory time/temperature conditions, it can be difficult to determine where, in the storage/transport chain, these unsatisfactory conditions have occurred. The result is that it is also difficult to determine who will be liable to meet possible claims for compensation.

The object of the present invention is to solve this problem by providing an enzymatic indicator whose indication can be discontinued at any desired point of time. As a result, a supplier for example would be able to prove, by discontinuing the indication displayed by an indicator applied to the product, that the product was not subjected to unsatisfactory conditions while in his care. In this context it should be observed that the indicator according to the present invention is not primarily intended as a replacement for earlier indicators but rather as a supplement to them. Thus, the indicator according to the present invention is preferably applied to the product together with a prior art indicator which, as stated above, is intended to enable the consumer to establish that the product has been handled in a satisfactory manner, while the indicator according to the present invention is intended to enable the manufacturer, supplier or any other person involved, to prove that he has handled the product in the correct manner. If more than one link in the chain precedes the sale of the product to the consumer, the corresponding number of indicators according to the present invention can be applied to the product so that each link has its own indicator.

The object of the present invention is achieved by providing an enzymatic indicator which, apart from aqueous liquid, contains as active substances enzyme, a substrate influenced by the enzyme as a result of which reaction products are formed, and a pH indicator for indicating the resultant reaction products. The component parts of the indicator are enclosed in a surrounding plastic envelope. According to the invention, the enzyme is bound to a solid carrier and the surrounding plastic envelope is sealable by means of pressure and preferably also heat so that the enzyme can be separated from at least a portion of the remaining component parts of the indicator by sealing the plastic envelope.

These objects and advantages of the invention will be more fully described in the following description, reference being had to the accompanying diagrammatic drawing.

Figure 1:
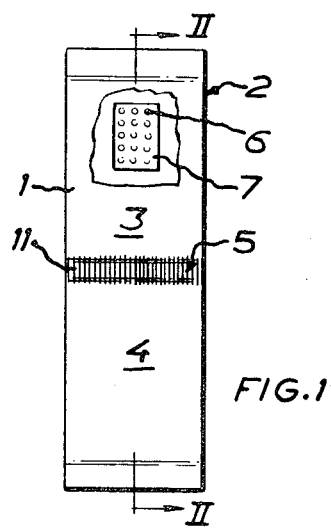
FIG. 1 is a plan view of an indicating device according to the invention, in the inactive state, part of the envelope having been removed to show its interior details.
Figure 2:
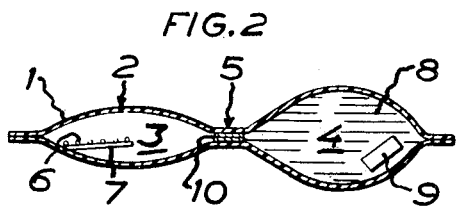
FIG. 2 is a cross-sectional view along the line II—II of the indicating device in FIG. 1.
Figure 3:
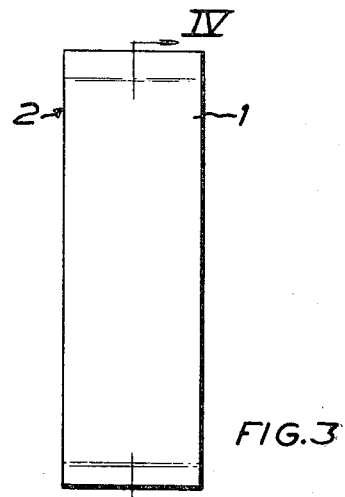
FIG. 3 is a plan view of the indicating device in FIG. 1, in the activated state.
Figure 4:
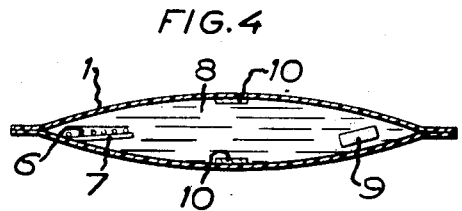
FIG. 4 is a cross-sectional view along the line IV—IV of the indicating device in FIG. 3.
Figure 5:
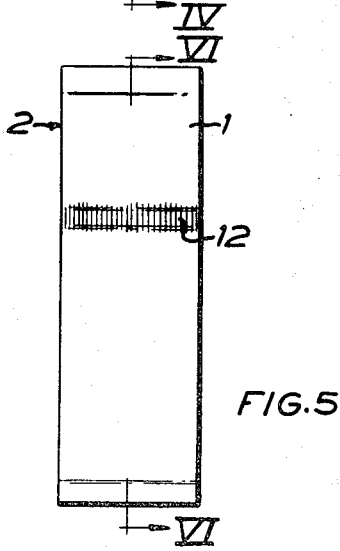
FIG. 5 is a plan view of the indicating device in FIG. 1, in the deactivated state.
Figure 6:
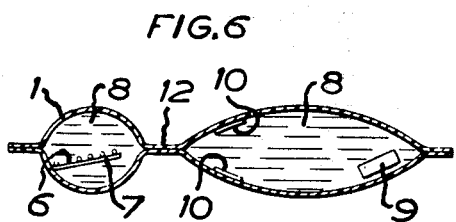
FIG. 6 is a cross-sectional view along the line VI—VI of the indicating device in FIG. 5.

According to a preferred embodiment of the invention, as shown in the drawings, the surrounding plastic envelope 1 forms a container 2 divided into two compartments 3, 4 by means of a frangible seal 5. The active substances of the indicator are divided up into the compartments 3, 4 such that one compartment 3 contains the enzyme 6 bound to the solid carrier 7, while the other compartment 4 contains the substrate 8 and the pH indicator 9 (see FIGS. 1 and 2). The seal 5 is created preferably by applying an adhesive 10 of the so-called "peel lacquer" type to a narrow portion or line 11 transversely across the opposite side surfaces, that is to say, on the inside of the plastic envelope 1. In the production of the container 2 from the plastic envelope 1 the enzyme 6 bound to the carrier 7 is arranged on one side of the adhesive line 11 and the substrate 8 and pH indicator 9 on the other side of the adhesive line 11. The opposite surfaces of the plastic envelope 1 are then pressed together in the region of the adhesive line 11, during application of heat and pressure. As a result, the adhesive 10 forms a seal separating the enzyme 6 bound to the carrier 7 from the substrate 8 and the pH indicator 9. By using an adhesive of the above stated type the thus obtained seal is not permanent. Instead, by exerting pressure against one or both of the formed compartments 3, 4 the seal is broken so that communication is established between both compartments 3, 4 (see FIGS. 3 and 4). As a result, the indicator can, after manufacture but prior to use, be stored in the inactive state without the risk that any indication occur. When the indicator is later applied to its intended location, it is only necessary to exert pressure, in the above described manner, on the indicator to establish communication between the compartments 3, 4 and activate the indicator. On deactivating the indicator (see FIGS. 5 and 6), that is to say, when the indication is to be discontinued at a desired point of time, the seal necessary for the deactivation is preferably produced by applying pressure and heat along a line 12 separate from the earlier seal line 11 to produce the two compartments, thereby creating maximum tightness of the new seal. It is also possible to produce the necessary seal simply by applying presssure to compress the opposite side surfaces of the plastic envelope, for example, by applying a clamp which mechanically compresses the opposite side surfaces the enzyme from at least a portion of the substrate and pH indicator.

For better understanding, the invention will be illustrated by the following non-limitative Examples.

EXAMPLE 1

The enzyme pancreas lipase (pancreas lipase PL III from Worthington Biochemical Corp., N.J., USA) was bound to a carrier consisting of 1 cm$^2$ piece of nylon fabric of nylon 6 ("Floater ¾oz" from Hood Sailmakers, Marblehead, USA) by means of glutaraldehyde (in this context reference is made, for such a binding process, to Quiocho, F.A. and Richards, F.M., Proc. Natl. Acad, Sci, U.S., 52, 833 (1964)). As a result, the pancreas lipase was fixedly bound to the nylon carrier whereby a carrier-bonded enzyme insoluble in water was obtained.

A substrate solution was then prepared, the solution consisting of 1% tricaproin in acetone added to a solution of water and 43.5 % glycerol. An indicator paper with a pH indicator (Nicht Blutend Spezialindikator pH 6.5–10.0, Artikel 9543 from Merck AG, Darmstadt, Federal Republic of Germany) was added to the thus-produced substrate solution.

Use was made, for the plastic envelope, of a three-layer plastic sheeting which consisted, taken in order from the outer face towards the indicating substances, of a polyester layer of the type Mylar, a polyvinylidene chloride layer of the type Saran, and a layer of low density (LD) polyethylene. This sheeting may be obtained from Akerlund & Rausing AB, Lund, Sweden and is marketed under the trade name AR MK 50.

The carrier-bonded enzyme was then applied to the plastic sheeting and fixedly attached thereto by applying heat and pressure to one corner of the nylon fabric which melted in this region and fused to the plastic sheeting. A container in accordance with the above was then formed from the plastic sheeting, and the substrate solution with the pH indicator was introduced into the container, the carrier-bonded enzyme and the substrate solution being separated by heat-sealing of the container at a temperature of from 130° to 140°C along a previously applied line of "peel-lacquer". For purposes of control a strip of the above-stated indicator paper was inserted also into the compartment having the carrier-bonded enzyme. The finished indicator was then ready for use.

In order to activate the indicator the compartment with the substrate solution was compressed, whereupon the seal separating the carrier-bonded enzyme from the substrate solution broke thus establishing communication between the enzyme and the substrate solution and starting the indication process. Once the indication had proceeded until a clear colour change had become apparent in both of the pH indicator strips, the indication was discontinued by creating a seal by means of a compression heat-sealing tool at a temperature of from 125° to 135°C. The seal separated the carrier-bonded enzyme and the control indicator paper from the main part of the remainder of the indicator (that is to say, the main part of the substrate solution as well as the second indicator paper). The enzyme was now prevented from acting upon the separated part of the substrate solution, and it was possible to establish, after storage of the indicator at room temperature for a long period, that no further colour change had taken place in the pH indicator in the part of the substrate solution which was separated from the enzyme, while the part still in contact with the enzyme produced a continued colour change in the control indicator paper.

EXAMPLE 2

The experiment according to Example 1 was repeated, with the exception that use was made, as the plastic sheeting, of a sheeting of fluorinated hydrocarbon polymer commercially designated Aclar from the Allied Chemical Corp., USA. Apart from the fact that it is heat-sealable, this sheeting is also gas and liquid-tight. A result corresponding to that of Example 1 was obtained.

EXAMPLE 3

The experiment according to Example 1 was repeated, with the exception that use was made, for the plastic sheeting, of a two-layer laminated sheeting of polyvinylidene chloride (Saran) and high density (HD) polyethylene. This latter layer was heat-sealable and was therefore arranged innermost. A result corresponding to that of Example 1 was obtained.

The invention has been described above with reference to particular preferred embodiments, but it is to be understood that different modifications may be made within the spirit and scope of the present invention. Thus, the coating with an adhesive of the "peel-lacquer" type can be replaced by any other type of adhesive or tacky coating which, on application of pressure and possibly also heat, provides the desired frangible seal. If the indicator is produced simultaneously with the product it is intended to indicate, it is not necessary to provide any initial frangible seal. Instead, the indicator is directly attached to the product so that indication can thus begin immediately. Moreover, the invention is, of course, not restricted to the enzyme and substrate cited by way of example, it being possible to use other known combinations of enzyme/substrate. Similarly, the carrier and coupler (glutaraldehyde) cited by way of example are merely illustrative of carriers and couplers, and it is, of course, possible to use other carrier materials known within the art and to couple the enzyme to the carrier by means of other per se known couplers and coupling processes.

What I claim and desire to secure by Letters Patent is:

1. In a time and temperature-dependent enzymatic indicating device for indicating the storage conditions of storage-sensitive perishable products comprising an aqueous liquid containing an enzyme, a substrate capable of being acted on by said enzyme to produce reaction products, and a pH indicating substance which changes color for indicating a change in pH resulting from action of said enzyme on the substrate, said aqueous liquid being enclosed in a surrounding plastic envelope having opposed inner surfaces, the improvement comprising the time and temperature-dependent enzymatic indicating device being operable to stop color change of said pH indicating substance by having the enzyme bound to a solid carrier and having the opposed inner surfaces of said surrounding plastic envelope comprise a layer of a material which is sealable by means of pressure whereby said indicating device is divisible into separate compartments including at least one compartment free from enzyme wherein further change of said indicating substance can not continue.

2. The indicating device according to claim 1, characterized by the fact that said enzyme is initially disposed in a first compartment, while said substrate and said pH indicating substance are initially disposed in another compartment, said compartments being separated by means of a frangible seal interconnecting the opposite walls of said plastic envelope.

3. The indicating device according to claim 1, characterized by the fact that said enzyme is pancreas lipase.

4. The indicating device according to claim 1, characterized by the fact that said carrier is nylon.

5. The indicating device according to claim 1, characterized by the fact that said enzyme is bound to said carrier by means of glutaraldehyde.

6. The indicating device according to claim 1, characterized by the fact that said substrate is tricaproin.

7. The indicating device according to claim 1, characterized by the fact that said plastic envelope consists of a three-layer plastic sheeting comprising one layeer of polyester, one layer of polyvinylidene chloride, and one layer of low density polyethylene.

8. The indicating device according to claim 1, characterized by the fact that said plastic envelope consists of a two-layer plastic sheeting comprising one layer of polyvinylidene chloride and one layer of high density polyethylene.

9. The indicating device according to claim 1, characterized by the fact that said plastic envelope consists of fluorinated hydrocarbon polymer sheeting.

* * * * *